United States Patent [19]
DeLoach et al.

[11] Patent Number: 5,308,615
[45] Date of Patent: May 3, 1994

[54] PROBIOTIC FOR CONTROL OF SALMONELLA

[75] Inventors: John R. DeLoach; Donald E. Corrier, both of College Station, Tex.; Arthur Hinton, Jr., Auburn, Ala.

[73] Assignee: The United States of America as represented by the Secretary of Agriculture, Washington, D.C.

[21] Appl. No.: 822,505

[22] Filed: Jan. 17, 1992

[51] Int. Cl.$^5$ .............................................. C12N 1/20
[52] U.S. Cl. ............................. 424/93 C; 424/93 H; 424/93 J; 426/2
[58] Field of Search ................. 424/93 C, 93 H, 93 J; 426/2

[56] References Cited

U.S. PATENT DOCUMENTS

| | | | |
|---|---|---|---|
| 3,956,482 | 5/1976 | Hahn et al. | 424/93 C |
| 4,138,498 | 2/1979 | Das | 424/93 C |
| 4,335,107 | 6/1982 | Snoeyenbos et al. | 424/93 |
| 4,689,226 | 8/1987 | Nurmi et al. | 424/93 |
| 4,794,080 | 12/1988 | Mays et al. | 435/42 |

OTHER PUBLICATIONS

Szylit et al., Reprod. Nutr. Develop 28(6A); 1455–1464 (1988).
Corrier, D. E. et al., "Decreased Salmonella Colonization in Turkey Poults Inoculated With Anaerobic Cecal Microflora and Provided Dietary Lactose", 1991 Poultry Science, 70, pp. 1345–1350.
Hinton, Arthur et al., "Environment and Health Comparison of the Efficacy of Cultures of Cecal Anaerobes as Inocula to Reduce Salmonella typhimurium Colonization in Chicks With or Without Dietary Lactose", 1991 Poultry Science, 70, pp. 67–73.
Corrier, Donald E. et al., "Effect of Anaerobic Cecal Microflora and Dietary Lactose on Colonization Resistance of Layer Chicks to Invasive Salmonella enteritidis", Avian Disease, 35, 1991, pp. 337–343.
Hinton, Arthur Jr., et al., "In Vitro Inhibition of the Growth of Salmonella typhimurium by Bacteria Isolated From the Cecal Contents of Mature Chickens", Abstracts, Twelfth Annual Meeting of the Southern Poultry Science Society, Atlanta, Georgia, Jan. 28–29, 1991.
Hinton, A. Jr., et al., "Inhibition of the Growth of Escherichia coli O15:H7 by Bacteria Isolated from Chickens", Abstracts, IFT Annual Meeting & Food Expo, Dallas, Texas, Jun. 1–5, 1991.
Hinton, Arthur Jr., et al., "In Vitro Inhibition of the Growth of Salmonella typhimurium, and Escherichia coli O157:H7 by Bacteria Isolated from the Cecal Contents of Adult Chickens", Journal of Food Protection, vol. 54, Jul. 1991.
Hinton, Arthur Jr., et al., "Biological Control of Salmonella typhimurium in Young Chickens", Avian Diseases, 34, 1990, pp. 626–633.
Corrier, Donald E., et al., "Effect of Dietary Lactose on Cecal pH Bacteriostatic Volatile Fatty Acids, and Salmonella typhimurium Colonization of Broiler Chicks", Avian Diseases, 34, 1990, pp. 617–625.

(List continued on next page.)

Primary Examiner—Douglas W. Robinson
Assistant Examiner—Jean C. Witz
Attorney, Agent, or Firm—M. Howard Silverstein; John D. Fado; Randall E. Deck

[57] ABSTRACT

Salmonella colonization of fowl may be effectively controlled or inhibited using a defined composition of anaerobic bacteria (i.e., probiotic). the probiotic includes a first culture of substantially pure anaerobic bacteria effective for fermenting lactic acid to produce volatile organic acids including acetic, propionic and/or butyric acids. A second culture of at least one anaerobic bacteria effective for fermenting carbohydrates to produce lactic acid is also employed in combination with the above-mentioned first cuture. Suitable organisms for use in this first culture include bacteria of the genera Veillonella, Megasphaera, and mixtures thereof. These first and second cultures are administered to the subject fowl in amounts effective for inhibiting Salmonella colonization thereof. In one embodiment, the above-mentioned probiotic may be combined with a conventional feed, providing a novel feed product which may be orally ingested by the fowl.

39 Claims, No Drawings

OTHER PUBLICATIONS

Corrier, Donald E., et al., "Effect of Dietary Lactose on Salmonella Colonization of Market-Age Broiler Chickens", *Avian Diseases*, 34, 1990, pp. 668–676.

Ziprin, Richard L., et al., "Intracloacal *Salmonella typhimurium* Infection of Broiler Chickens: Reduction of Colonization with Anaerobic Organisms and Dietary Lactose", *Avian Diseases*, 34, 1990, pp. 749–753.

Oyofo, Buhari A., et al., "Effect of Carbohydrates on *Salmonella typhimurium* Colonization in Broiler Chickens", *Avian Diseases*, 33, 1989, pp. 531–534.

Stavric, S., et al., "Competitive Exclusion of Salmonella from Newly Hatched Chicks by Mixtures of Pure Bacterial Cultures Isolated from Fecal and Cecal Contents of Adult Birds", *Journal of Food Protection*, vol. 48, No. 9, Sep. 1989, pp. 778–782.

Hinton, M., et al., "Salmonella Control in Poultry: The Need for the Satisfactory Evaluation of Probiotics for this Purpose", *Letters in Applied Microbiology*, 13, 1991, pp. 49–50.

PROBIOTIC FOR CONTROL OF SALMONELLA

BACKGROUND OF THE INVENTION

1. Field of Invention

This invention relates to a defined probiotic for the control of Salmonella colonization in fowl, particularly chickens.

Despite the efforts of researchers and public health agencies, the incidence of human salmonellosis has increased over the past 20 years. The number of actual reported cases of human Salmonella infection exceeds 40,000 per year. However, the Communicable Disease Center estimates that the true incidence of human Salmonella infections in the U.S. each year may be as high as 2 to 4 million. Animal food products, including poultry, remain the principal source of human infection.

2. Description of the Prior Art

Considering the widespread presence of Salmonella in the environment, it is unlikely that poultry can be completely protected from Salmonella exposure. Therefore, researchers have continued to investigate means of increasing resistance to colonization in poultry exposed to Salmonella. Studies have focused on the evaluation of vaccines, establishment of protective normal intestinal flora, and the identification of feed additives that will inhibit Salmonella growth and colonization. The role of host immunity against Salmonella colonization is unclear, and it also remains uncertain if stimulation of immune responses will effectively enhance colonization resistance. Experimental vaccines have not proven to be consistently effective.

It is well documented that normal intestinal microflora increase resistance against Salmonella colonization. Oral inoculation of young chicks with anaerobic bacterial cultures of microflora, also known as probiotics (defined as bacterial cultures which have a beneficial effect on the animal to which they are administered), prepared from the cecal contents or fecal droppings of mature chickens has proven to effectively reduce Salmonella colonization (Snoeyenbos et al., Avian Dis. 23:904-913 (1979), Schneitz et al., Acta Pathol. Microbiol. Scand. Sect. B., 89:109-116, (1981), and Stavric et al., J. Food Prot., 48:778-782, (1985)). Conversely, poultry rearing practices that prevent chicks from becoming colonized by these cecal anaerobes make the chicks more susceptible to Salmonella colonization (Pivnick et al., J. Food Prot., 44:909-916, (1981)). These probiotics may decrease Salmonella colonization by rapidly colonizing the intestinal tract of the young chicks (Pivnick et al., ibid), by competing for attachment sites on the intestinal wall (Snoeyenbos et al., ibid), or by producing bacteriostatic or bactericidal short-chained volatile fatty acids (Barnes et al., J. Hyg. Camb., 82:263-283, (1979) and Am. J. Clin. Nutr., 33:2426-2433, (1980), Corrier et al., Avian Dis., 34:668-676, (1990) and Avian Dis., 34:626-633, (1990), and Hinton et al., Avian Dis., 34:626-633, (1990)) that inhibit the growth of enteropathogens.

However, only cultures of normal microflora that contain a mixed population of several hundred different micro-organisms have proven to effectively inhibit Salmonella growth. Establishment of normal intestinal flora in day-old chicks using mixed cultures of micro-organisma has been widely used to control Salmonella colonization in several European countries. Yet, because of the undefined number and types of micro-organisms present in mixed cultures, the system has not been widely accepted in the United States. One drawback to the widespread use of this method has been the fact that the composition of the product cannot be standardized, and thus the product cannot be stored or produced on a large scale without changes in composition and effectiveness. Also, because the starting material is always the intestinal content of an adult fowl, the product may contain pathogenic viruses, bacteria, or parasites, which may be dangerous to the health of the chicks. Further still, the U.S. Food & Drug Administration has recently required that all undefined cultures must be approved.

Lactose and other milk sugar products added to the feed or water of chicks have recently been reported to enhance resistance against Salmonella colonization (Oyofo et al., Avian Dis., 33:531-534, (1989) and Poultry Sci, 68:1357-1360, (1989), Corrier et al., ibid, and Hinton et al., ibid.). Dietary lactose increases the acidity of the cecal contents and influences the growth and fermentation products of normal intestinal microflora. Lactose supplemented diets may also enhance Salmonella colonization resistance by increasing the bacteriostatic action of short chain volatile fatty acids such as acetic, propionic, and butyric acids, produced by some normal intestinal bacteria (Corrier et al., ibid, Hinton et al., ibid).

Resistance to Salmonella colonization in chicks has also further been increased when the chicks are provided the combination of dietary lactose and cultures of cecal anaerobes grown in a lactose containing broth (Corrier et al., ibid, Hinton et al., ibid).

SUMMARY OF THE INVENTION

We have now discovered a defined probiotic or composition of anaerobic bacteria effective for controlling or inhibiting Salmonella colonization of fowl. The probiotic includes a first culture of substantially pure anaerobic bacteria effective for fermenting lactic acid to produce volatile organic acids including acetic, propionic and/or butyric acids. A second culture of at least one anaerobic bacteria effective for fermenting carbohydrates to produce lactic acid is also employed in combination with the above-mentioned first culture. Suitable organisms for use in this first culture include bacteria of the genera Veillonella, Megasphaera, and mixtures thereof. These first and second cultures of the probiotic are administered to the subject fowl in amounts effective for inhibiting Salmonella colonization thereof. In one embodiment, the above-mentioned probiotic may be combined with a conventional feed, providing a novel feed product which may be orally ingested by the fowl.

In accordance with this discovery, it is an object of this invention to provide an improved method and composition for controlling Salmonella colonization in fowl.

A further object of this invention is to provide defined cultures of anaerobic bacteria for controlling Salmonella colonization in fowl which may be easily standardized.

Other objects and advantages of this invention will become obvious from the ensuing description.

DETAILED DESCRIPTION OF THE INVENTION

According to this invention, a probiotic is provided which includes a first culture of substantially pure anaerobic bacteria effective for fermenting lactic acid to produce volatile organic acids including acetic, propionic and/or butyric acids, in combination with a second culture of at least one anaerobic bacteria effective for fermenting carbohydrates to produce lactic acid. When administered to fowl, the probiotic is effective for controlling Salmonella colonization thereof. The invention may be practiced with any type of fowl, including but not limited to poultry such as chickens, turkeys, ducks, quail and geese.

Suitable anaerobic bacteria utilized in the first culture of the probiotic include substantially pure bacteria of the genera Veillonella, Megasphaera and mixtures thereof, which are effective for producing volatile organic acids including acetic, propionic, and/or butyric acids. Although the bacteria to be used may be obtained from known strains of Veillonella and Megasphaera adapted to the fowl by passage therethrough, in accordance with the preferred embodiment, they are isolated from the fecal droppings or cecal contents of adult fowl using techniques conventional in the art. Regardless of the source, the bacteria are propagated by anaerobic culture, and selected for the ability to produce one or all of the above-mentioned volatile organic acids, such as described by Hinton et al. (J. Food Prot., vol. 54, no. 7, pages 496–501, (July 1991), the contents of which are incorporated by reference herein). Particularly preferred anaerobes for use in the first culture are *Veillonella parvula*, and *Metasphaera elsdenii*.

The anaerobic bacteria of the second culture of the probiotic should be effective for fermenting carbohydrates to produce lactic acid. While these bacteria of the second culture may be used in crude or impure form, in the preferred embodiment, substantially pure cultures are used to aid in standardization of the probiotic. As with the first culture, the bacteria to be used in the second culture may be obtained from known strains of anaerobic bacteria adapted to the fowl by passage therethrough. However, in the preferred embodiment, the bacteria are isolated from the fecal droppings or cecal contents of adult fowl using techniques conventional in the art. For this second culture, the bacteria are again propagated by anaerobic culture, and selected for the ability to ferment carbohydrates to produce lactic acid, such as described by Hinton et al., (1991, ibid). Without being limited thereto, preferred anaerobic bacteria for use in the second culture may be of the genera Streptococcus, Enterococcus, and Lactobacillus, with *Streptococcus intermedius, Streptococcus morbillum, Enterococcus durans*, and *Lactobacillus acidophilus* being particularly preferred. Although only on of these bacteria may be used in the second culture of the probiotic, it is preferred to use at least two or three, and especially all of the above-mentioned strains for enhanced inhibition of Salmonella colonization.

Some or all of the strains of the bacteria of this invention may also be optionally selected for the ability to adhere to the epithelial cells of the alimentary tract of the subject fowl in accordance with the technique of Nurmi et al, U.S. Pat. No. 4,689,226, the contents of which are incorporated by reference herein.

The probiotic of this invention may be obtained by propagating the bacteria of the first and second cultures in a suitable culture medium using anaerobic culture techniques conventional in the art. The bacteria may be cultured in combination, or preferably in separate culture media for ease of standardization. The final concentration of each bacteria should be between about $10^8$ to $10^9$ organisms/ml prior to combination. In accordance with the preferred embodiment, we have discovered that enhanced inhibition of Salmonella colonization is obtained when the ratio of the second culture to the first culture is between about 1:1 and about $1:10^{-8}$, and particularly at a ratio of about $1:10^{-2}$ on a volume:-volume basis. However, the practitioner skilled in the art will recognize that this ratio may vary depending upon the culture medium used, the relative ages of the cultures and their viability.

Following this propagation, the first and second cultures may be administered to the subject fowl singly or in combination. Optionally, the cultures may be further formulated with a suitable carrier including, but not limited to lactose or skim milk, or combined with a small amount of feed for use as a premix. The cultures may also be freeze dried for storage stability and ease of handling. Such freeze dried cultures may be directly administered to the fowl or in the alternative reconstituted prior to use. Of special note, one or all of the bacteria, and particularly the first culture, may be encapsulated using techniques conventional in the art, including, but not limited to encapsulation in an alginate gel. Without wishing to be bound be theory, it is believed that encapsulation in this manner may prevent bacteria in the first culture from reducing the concentration of lactic acid in the upper intestinal tract to undesirable levels. It may also protect the bacteria and allow them to reach the ceca, where lactic acid utilization by the first culture is desirable.

The probiotic of this invention may also be combined with other adjuvants conventional or known in the art for the treatment of fowl and particularly for the inhibition of enteropathogens. Suitable adjuvants include, for example, coccidiostats such as monensin that are not effective against gram positive organisms, and/or lactose.

While the probiotic of this invention is primarily administered or introduced to the alimentary tract by combining with the feed or water of the fowl followed by oral ingestion thereof, it is envisioned that it may also be injected directly into the gastrointestinal tract, or administered cloacally. In regard to the latter, the probiotic may be sprayed directly onto the anus of the fowl or applied to the pen floor litter whereupon it will contact the anal area through the course of normal activity of the fowl. Once contacted with the anal area, the probiotic will be introduced into the cloaca by reverse peristalsis.

Administration of the probiotic may be at any time during the life of the fowl. However, in the preferred embodiment the probiotic is administered to newly hatched fowl between about 1 to 14 days old.

The probiotic is administered in an amount effective to substantially inhibit the Salmonella colonization in the treated fowl, in comparison with untreated fowl. Suitable amounts may be readily determined by the practitioner skilled in the art, and will vary somewhat with the size of the animal.

The following examples are intended only to further illustrate the invention and are not intended to limit the scope of the subject matter which is defined by the claims.

EXAMPLE 1

Isolation of Bacteria

Cecal contents were removed from adult broilers and stored at $-70°$ C. as described in Hinton et al., (Avian Dis., 34:626–633, (1990)) the contents of which are incorporated by reference herein. Approximately 2 ml of the thawed cecal contents were added to 200 ml of modified Viande Levure (VL) broth. The composition of the broth was 10 g/l tryptose (Difco Laboratories, Detroit, Mich.); 5 g/l yeast extract (Difco); 5 g/l sodium chloride (J.T. Baker, Phillipsburg, N.J.); 2.4 g/l beef extract (Difco); 0.4 g/l L-cysteine hydrochloride (Sigma Chemical Co., St. Louis, Mo.); 2.5 g/l dextrose (ICN Biochemicals, Cleveland Ohio); and 0.6 g/l Bacto agar (Difco). Modified VL agar was made by increasing the agar concentration to 1.2%.

The inoculated broth was incubated in an anaerobic chamber (Coy Laboratory Products, Ann Arbor, Mich.) at 37° C. for 18–24 hours. Bacteria were isolated from the broth by plating serial dilutions of the broth onto VL agar and again incubating anaerobically at 37° C. for 18–24 hours. Tubes of Reinforced Clostridial Medium (RCM) (Unipath Co., Oxoid Division. Ogdensburg, N.Y.) were inoculated with the isolates and incubated anaerobically at 37° C. for 18–24 hours. Cultures were maintained by transferring to fresh RCM at 1–2 week intervals, incubating, and storing at ambient temperature in the anaerobic chamber.

Lactic Acid Producing Bacteria

Separate tubes containing modified VL broth were inoculated with the isolates. The inoculated tubes were incubated anaerobically at 37+ C. for 18–24 hours. After incubation the growth media was analyzed by gas chromatography with a Shimadzu Gas Chromatography GC-9A (Shimadzu Corp., Columbia, Md.) to determine the level of lactic acid produced as in Hinton et al., ((1990, ibid). The two isolates that produced the greatest concentration of lactic acid were retained.

Another isolate producing lactic acid was recovered using similar techniques, but the isolation media was a modified VL broth in which lactose was substituted for glucose, and the pH of the media was adjusted to 4.0.

Volatile Organic Acid Producing Bacteria

To select for bacteria that can convert lactic acid into volatile organic acids, a lactic acid based media was prepared by substituting 0.25% L-lactic acid, lithium salt (Sigma) for dextrose in the modified VL media. Each isolate obtained in the above-described procedure was added to separate tubes of this media, and the tubes were incubated anaerobically at 37° C. for 18–24 hours. After incubation, the growth media of these isolates were also analyzed by gas chromatography. The isolate that produced the greatest amount of volatile organic acids (acetic and propionic acid) was retained.

Lactic Acid Producing and Starch-Hydrolyzing Bacteria

A fourth bacterium effective for producing lactic acid and also hydrolyzing starch was also isolated. Serial dilutions of cecal contents incubated in modified VL broth were plated on a starch based agar media prepared by substituting 0.30% soluble starch (Sigma) for dextrose in the modified VL agar and adding 0.5% $K_2HPO_4$. Tubes of RCM and fresh plates of the starch media were each inoculated with morphologically different isolates picked from the incubated plates. After incubation of the tubes and plates, the plates were flooded with Gram's iodine solution (Difco). The isolates that hydrolyzed the starch were selected by examining the flooded plates for zones of clearing around colonies on the agar. One starch-hydrolyzing bacterium was isolated. The bacterium was grown and stored in the anaerobic chamber in a starch medium containing 10 g/l tryptone (Difco); 10 g/l yeast extract (Difco); 5 g/l $K_2HPO_4$ (Sigma); and 3 g/l soluble starch (Difco). The starch-hydrolyzing bacterium was also analyzed for the ability to produce lactic acid as described hereinabove.

Identification of the Isolates

The Gram reaction and the oxygen requirements of all of the isolates were determined. Further identification was done with the BBL Minitek Numerical Identification System, Anaerobe II (Becton Dickinson Microbiology System, Cockeysville, Md.) and the Microrings AN antibiotic discs (Medical Wire & Equipment Co., USA, Victory Gardens, N.J.). Other fermentation products of the bacteria were identified by gas chromatography after the isolates were incubated anaerobically at 37° C. for 48 hours in polypeptone-yeast extract medium with 0.1% glucose (Association of Official Analytical Chemist, 1976, Bacteriological Analytical Manual, Washington, D.C.).

The lactic acid producing isolates were identified as *Enterococcus durans* (designated as strain CA240), *Lactobacillus acidophilus* (designated as strain CA255), and *Streptococcus morbillum* (designated as strain CA331). The starch-hydrolyzing and lactic acid producing isolate was identified as *Streptococcus intermedius* (designated as strain CA502). The volatile organic acid producing isolate was identified as *Veillonella parvula* (designated as strain CA126).

EXAMPLE 2

Reduction of Cecal Colonization by *Salmonella typhimurium*

The above-identified lactic acid producing isolates, *L. acidophilus, E. durans, S. intermedius,* and *S. morbillum*, were grown in petri dishes containing reinforced clostridial agar (Unipath) in an anaerobic chamber (Coy) at 37° C. for 18–24 hours. The volatile organic acid producing isolate, *V. parvula*, was grown in petri dishes containing modified VL agar supplemented with 13 g/l sodium lactate (Sigma). The pH of the media was adjusted to 7.2 with 1.0 N sodium hydroxide and the media was autoclaved. The *V. parvula* was grown in this media in an anaerobic chamber (Coy) at 37° C. for 48 hours.

The bacteria were harvested from the plates using a solution of 0.85% sodium chloride (J.T. Baker) and 0.6% Bacto agar (Difco). Four ml of this solution were poured onto the surface of the bacterial growth, and a glass rod was used to scrape the bacteria from the agar. The suspension of *V. parvula* was diluted 100 fold in the sodium chloride-agar solution. Equal parts of the undiluted suspensions of *L. acidophilus, E. durans, S. morbillum,* and *S. intermedius,* and the diluted suspension of *V. parvula* were mixed in the anaerobic chamber in ratios (volume:volume) varying from 1:1 to $1:10^{-8}$ with treatment 1 being a control. One part of the mixed bacteria suspension and one part of a sterile solution of 20% skim milk (Difco) were combined. This bacteria-skim milk mixture was transferred into lyophilization bottles, frozen at −70° C. for approximately 1 hour, and freeze-dried.

One gram of the lyophilized cultures was added to 999 g of chicken feed and thoroughly mixed therewith. Seventy two chicks were divided into 6 groups of 12 chicks each and provided the mixed feeds as indicated in Table 1 on day 1. On day 2 the chicks were challenged with $10^4$ *S. typhimurium*, and then sacrificed on day 8. The concentration of *S. typhimurium* in the cecal contents of the chicks was determined as described by Ziprin et al. (Avian Diseases, 34:749–753, (1990), the contents of which are incorporated by reference herein). The results are shown in Table 1.

EXAMPLE 3

Reduction of Cecal Colonization by *Salmonella typhimurium*

The procedure of Example 2 was repeated with another population of newly hatched chicks. The results are shown in Table 2.

The results shown in Tables 1 and 2 demonstrate that all treatments with the probiotics were effective in inhibiting Salmonella colonization in the chicks. The treatment number 3, having a ratio of the second culture to the first culture of $1:10^{-2}$ on a volume:volume basis, was particularly effective, greatly reducing the numbers of chicks infected and reducing the average concentration of *S. typhimurium* by more than 4 logs.

It is understood that the foregoing detailed description is given merely by way of illustration and that modifications and variations may be made therein without departing from the spirit and scope of the invention.

TABLE 1

| Treatment group | Average log S. typhimurium | No. infected |
| --- | --- | --- |
| 1 | 5.36 | 10/10 |
| 2 | 3.47 | 8/10 |
| 3 | 1.25 | 3/10 |
| 4 | 2.70 | 7/10 |
| 5 | 4.52 | 9/10 |
| 6 | 2.57 | 7/10 |

TABLE 2

| Treatment group | Average log S. typhimurium | No. infected |
| --- | --- | --- |
| 1 | 6.74 | 10/10 |
| 2 | 4.51 | 8/10 |
| 3 | 3.80 | 8/10 |
| 4 | 4.79 | 9/10 |
| 5 | 5.21 | 9/10 |
| 6 | 5.97 | 10/10 |

We claim:

1. A composition for inhibiting Salmonella colonization of fowl comprising:
   (a) a culture of substantially pure Veillonella effective for fermenting lactic acid to volatile organic acids and
   (b) a culture of at least two strains of anaerobic bacteria effective for fermenting carbohydrates to produce lactic acid, said strains of anaerobic bacteria effective to produce lactic acid being selected from the group consisting of *Streptococcus intermedius, Streptococcus morbillum, Enterococcus durans* and *Lactobacillus acidophilus.*

2. A composition as described in claim 1, wherein said Veillonella is *Veillonella parvula.*

3. A composition as described in claim 1, comprising at least three of said anaerobic bacteria effective to produce lactic acid.

4. A composition as described in claim 1, comprising all of said anaerobic bacteria effective to produce lactic acid.

5. A composition as described in claim 1, further comprising lactose.

6. A composition as described in claim 1, further comprising a coccidiostat that is not active against gram positive bacteria.

7. A composition as described in claim 1, further comprising a carrier.

8. A composition as described in claim 1, wherein said Veillonella are encapsulated.

9. A composition as described in claim 1, wherein the ratio of the culture of said anaerobic bacteria effective to produce lactic acid to the culture of said Veillonella is between about 1:1 and about $1:10^{-8}$.

10. A composition as described in claim 9, wherein said ratio is about $1:10^{-2}$.

11. A feed product comprising an animal feed in combination with said composition of claim 1.

12. A method for inhibiting Salmonella colonization of fowl comprising administering to said fowl:
    (a) a culture of substantially pure Veillonella effective for fermenting lactic acid to volatile organic acids and
    (b) a culture of at least two strains of anaerobic bacteria effective for fermenting carbohydrates to produce lactic acid, said strains of anaerobic bacteria effective to produce lactic acid being selected from the group consisting of Streptococcus, Enterococcus and Lactobacillus, in an amount effective for inhibiting Salmonella colonization of the intestine of said fowl.

13. A method as described in claim 12, wherein said fowl are poultry.

14. A method as described in claim 13, wherein said poultry are selected from the group consisting of chickens, turkeys, ducks, quail and geese.

15. A method as described in claim 14, wherein said poultry are less than about 14 days old.

16. A method as described in claim 12, wherein said Veillonella is *Veillonella parvula.*

17. A method as described in claim 12, wherein said anaerobic bacteria effective to produce lactic acid are selected from the group consisting of *Streptococcus intermedius, Streptococcus morbillum, Enterococcus durans* and *Lactobacillus acidophilus.*

18. A method as described in claim 17, wherein at least three of said anaerobic bacteria effective to produce lactic acid are administered to said fowl.

19. A method as described in claim 17, wherein all of said anaerobic bacteria effective to produce lactic acid are administered to said fowl.

20. A method as described in claim 12, further comprising administering lactose to said fowl.

21. A method as described in claim 12, further comprising administering a coccidiostat that is not substantially active against gram positive bacteria.

22. A method as described in claim 12, wherein said cultures are administered with a carrier.

23. A method as described in claim 12, wherein said Veillonella are encapsulated.

24. A method as described in claim 12, wherein the ratio of the culture of said anaerobic bacteria effective to produce lactic acid to the culture of said Veillonella is between about 1:1 and about $1:10^{-8}$.

25. A method as described in claim 24, wherein said ratio is about $1:10^{-2}$.

26. A method as described in claim 12, wherein said step of administering comprises orally administering said cultures to said fowl.

27. A method as described in claim 26, wherein said step of administering comprises providing said cultures in combination with feed for said fowl.

28. A method as described in claim 26, wherein said step of administering comprises providing said cultures in combination with water for said fowl.

29. A method as described in claim 12, wherein said step of administering comprises contacting said cultures with the cloaca of said fowl.

30. A composition as described in claim 1, further comprising a culture of substantially pure Megasphaera effective for fermenting lactic acid to volatile organic acids.

31. A composition as described in claim 30, wherein said Megasphaera is *Megasphaera elsdenii*.

32. A composition as described in claim 4, further comprising a culture of substantially pure Megasphaera effective for fermenting lactic acid to volatile organic acids.

33. A composition as described in claim 32, wherein said Megasphaera is *Megasphaera elsdenii*.

34. A method as described in claim 12, further comprising administering a culture of substantially pure Megasphaera effective for fermenting lactic acid to volatile organic acids.

35. A method as described in claim 34, wherein said Megasphaera is *Megasphaera elsdenii*.

36. A method as described in claim 12, wherein said Veillonella and said bacteria effective to produce lactic acid have been isolate from fecal droppings or cecal contents of adult fowl.

37. A method as described in claim 19, further administering a culture of substantially pure Megasphaera effective for fermenting lactic acid to volatile organic acids.

38. A method as described in claim 37, wherein said Megasphaera is *Megasphaera elsdenii*.

39. A composition for inhibiting Salmonella colonization of fowl comprising:
(a) a culture of substantially pure Veillonella effective for fermenting lactic acid to volatile organic acids and
(b) a culture of at least two strains of anaerobic bacteria effective for fermenting carbohydrates to produce lactic acid, said strains of anaerobic bacteria effective to produce lactic acid being selected from the group consisting of Streptococcus, Enterococcus and Lactobacillus,
wherein said Veillonella and said bacteria effective to produce lactic acid have been isolated from fecal droppings or cecal contents of adult fowl.

* * * * *